(12) United States Patent
Wong et al.

(10) Patent No.: US 6,978,945 B2
(45) Date of Patent: Dec. 27, 2005

(54) DISPENSING DEVICE

(75) Inventors: Kon Euan Wong, Glen Waverly (AU); Mark Simon Bayly, Eltham North (AU)

(73) Assignee: Acrux DDS Pty Ltd, (AU)

( * ) Notice: Subject to any disclaimer, the term of this patent is extended or adjusted under 35 U.S.C. 154(b) by 243 days.

(21) Appl. No.: 10/442,323

(22) Filed: May 21, 2003

(65) Prior Publication Data

US 2004/0050964 A1 Mar. 18, 2004

Related U.S. Application Data

(63) Continuation of application No. PCT/AU01/01560, filed on Nov. 30, 2001.

(30) Foreign Application Priority Data

Dec. 1, 2000 (AU) .................................... PR1845

(51) Int. Cl.[7] ................................................ B05B 1/28
(52) U.S. Cl. .................. 239/288.5; 239/326; 239/337; 239/350; 239/373; 239/499; 239/575; 222/402.13; 128/200.23; 604/289; 604/302; 604/310
(58) Field of Search ............................ 239/288, 288.3, 239/288.5, 103, 120, 121, 122, 333, 337, 239/373, 375, 326, 350, 499, 575; 222/108, 222/153.13, 153.14, 402.1, 402.11–402.14, 222/321.1, 321.7, 321.9; 604/301, 302, 289, 604/310; 128/200.14, 200.23

(56) References Cited

U.S. PATENT DOCUMENTS

| | | | | |
|---|---|---|---|---|
| 2,985,382 A | * | 5/1961 | Coplan | 239/288.5 |
| 3,191,867 A | * | 6/1965 | Lee | 239/288.5 |
| 3,306,252 A | * | 2/1967 | Knight et al. | 239/499 |
| 3,550,857 A | * | 12/1970 | Ahlberg | 239/288 |
| 3,887,115 A | * | 6/1975 | Petterson | 222/402.13 |
| 3,936,000 A | * | 2/1976 | Weyn | 239/288.5 |
| 4,292,966 A | * | 10/1981 | Mono et al. | 128/200.23 |
| 4,344,573 A | | 8/1982 | De Felice | |
| 6,113,008 A | * | 9/2000 | Arsenault et al. | 239/337 |

FOREIGN PATENT DOCUMENTS

| | | |
|---|---|---|
| AU | 139039 | 1/1948 |
| AU | 150729 | 8/1951 |
| AU | 463740 | 8/1975 |
| DE | 19809514 C1 | 12/1999 |
| WO | 93/24164 A1 | 12/1993 |
| WO | 98/06502 A1 | 2/1998 |

* cited by examiner

*Primary Examiner*—Steven J. Ganey
(74) *Attorney, Agent, or Firm*—Lerner, David, Littenberg, Krumholz & Mentlik, LLP

(57) ABSTRACT

Hand-held dispensing devices for dispensing and applying a substance to the skin of a host are described. The devices include a hollow body, a capsule mounted within the hollow body for containing the substance, a nozzle mounted within the hollow body communicating with the substance in the capsule, an actuator to cause metered quantities of the substance to be dispensed from the capsule through the nozzle, a shroud defining an exit space for receiving the substance emerging from the nozzle, and a cap detachably mounted on the shroud to selectively open and close the nozzle and thereby control escape of the substance from the capsule.

39 Claims, 4 Drawing Sheets

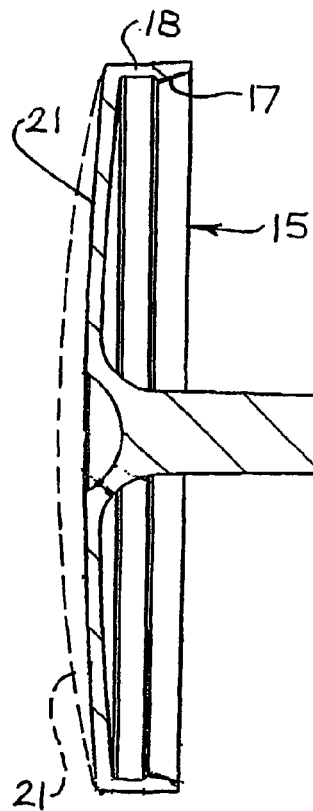
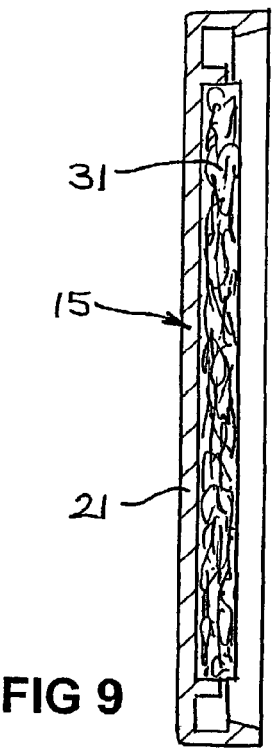
FIG 7
FIG 9
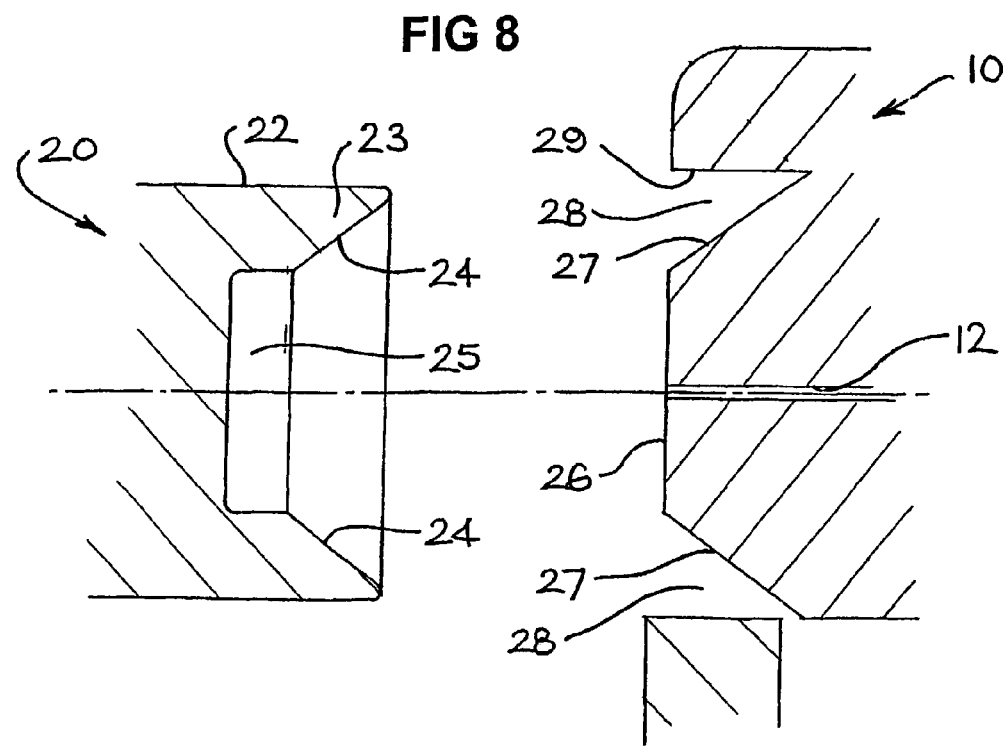
FIG 8

DISPENSING DEVICE

CROSS REFERENCE TO RELATED APPLICATIONS

The present application is a continuation of International Application No. PCT/AU01/01560, filed on Nov. 30, 2001, in the English language, the disclosure of which is incorporated by reference herein.

FIELD OF THE INVENTION

The present invention relates to a device for dispensing a substance, such as a pharmaceutical, medicinal, or therapeutic substance, and applying that substance to the skin of a host animal (e.g., a human). More particularly, the present invention relates to a device that is operable to dispense a metered quantity of a substance in the form of a spray or mist. More specifically, the present invention relates to transdermal and/or percutaneous delivery of substances, and in particular liquids containing a physiologically active agent.

BACKGROUND OF THE INVENTION

Drug delivery is the process of taking a drug and incorporating it into a dosage form to enable the drug to: (1) reach its target within the body; (2) be delivered at effective concentrations; (3) be absorbed in a timely manner; (4) not produce toxic side-effects; and (5) be in a convenient form for the patient. The transdermal route of drug delivery has been extensively explored as a means for effective drug delivery.

Traditionally, transdermal drug delivery systems have employed occlusive patch devices that are adhered to the skin for prolonged periods of time in order to deliver the drug across the skin and into the bloodstream at effective concentrations. However, transdermal patches suffer from major problems. Such problems include skin irritation at the site of application; poor cosmetic acceptability by the user; complex manufacturing processes; and limited flexibility for changing the dose applied. Adhesive transdermal matrix patches require complex and critical manufacturing steps, including: preparation of a drug solution; thermal blending of adhesive; precision coating onto the release liner; controlled drying of the patch (requires many in-process tests); laminating of the backing of the patch; die-cutting of different patch sizes; and final packing in foil-lined blister pack. (Jenkins A. W. Developing the FEMATRIX™ transdermal patch. Pharm. J. 1995, Vol 255, August 5 pp. 179–181).

There have been attempts to overcome such problems by reverting to the use of traditional non-occlusive topical vehicles, such as gels, creams and lotions, however the use of these vehicles for transdermal drug delivery has been constrained by their limited application to the full range of transdermal drug candidates due to a low transdermal flux. Gels, creams and lotions also suffer from messy application methods; poor dosage control during application; unacceptably long drying-times on the skin; and significant patient-to-partner transfer of the drug. Consequently, in U.S. Pat. No. 6,299,900 titled Dermal Penetration Enhancers and Drug Delivery System Involving Same, Reed et al., provide an improved non-occlusive, volatile:non-volatile transdermal drug delivery system that overcomes the above limitations of traditional transdermal drug delivery systems (eg., patches, gels, creams, lotions).

The foregoing problems have led to the development of devices for the controlled application of volatile:nonvolatile liquid formulations to the skin, such as that disclosed in U.S. Pat. No. 6,113,008, for example, which is a device for applying an occlusive spray-on bandage to the skin. That device suffers from the limitation of not providing means to prevent actuator nozzle blockage by the preferred film-forming aerosols during its normal use, and is also restricted by its axial nozzle orientation to practical application to the forearm only. That is unless the patient is willing to lie down during operation of the device for application to other traditional sites such as the abdomen, upper buttocks and thigh. Such an approach would then also pose the additional problem of a lack of dip-tube pick-up from the liquid reservoir, solutions to which are available, such as that described in U.S. Pat. No. 5,624,060, but which would add significant cost and complexity to the utility of the device disclosed by U.S. Pat. No. 6,113,008. That device also relies upon a vent in the dispensing shroud that is open to ambient air in order to prevent any pressure build-up when using the preferred pressurized aerosols, and that leads to spray drift with consequent loss of some of the dispensed substance.

U.S. Pat. No. 6,261,274 discloses another dispensing device that is reliant upon a distance-gauging means to control the distance and orientation of the actuator nozzle from the skin. That device suffers from the limitation of a likelihood of variable actuator nozzle angle and/or distance relative to the skin, notwithstanding the use of a flat surface at the end of the distance-gauging means that is pressed against the skin during use. That is because in practice, the surface area of this feature needs to be restricted in order to avoid encroachment upon the dispensed substance plume during normal use of the device. The typical length required for the distance-gauge would mean that little if any stabilizing effect is achieved during normal use, because the angle of the distance-gauge would be prone to angle changes due to normal compliance of the skin surface, a problem which is compounded by only having limited surface area of contact for the distance-gauge, as well as the leveraged effect that even a small change in the angle of the distance-gauge has on the distance and angle of the actuator nozzle relative to the skin. The device of U.S. Pat. No. 6,261,274 also suffers from the limitation that the patient needs to be able to assess the actual site at which the dispensed substance would be applied, which is a particular problem for application to the forearm, where the spacer leg could be placed on the skin but the substance then sprayed into the air, missing the skin altogether. The device therefore suffers from a high potential for variation in the surface area over which the dispensed substance is applied, and the possibility to miss the target application site.

Substance dispensing devices of the foregoing kind tend to suffer an unacceptable loss of the substance in the period between uses of the device. That loss is particularly evident in circumstances involving use of a volatile substance. Unintentional loss of the substance is wasteful, and can also interfere with the ability of the device to dispense an accurately metered quantity each time the device is operated. In that regard, accurate metering can be very important in some circumstances.

There is a need for a device having the ability to provide accurate and reproducible application of volatile:nonvolatile liquid formulations, such as those described in U.S. Pat. No. 6,299,900, at low volume levels, typically between 1 to 10 microliters per square centimeter of application area. There is also a need for a dispensing device having means for preventing loss-of-prime (or loss-of-residual dose)

It is one of the objects of the present invention to provide a substance dispensing device having means for preventing, or minimizing, unintentional loss of the substance. It is a further object of the present invention to provide a substance dispensing device that is able to dispense an accurately metered quantity of a substance during normal use. It is yet another object of the present invention to provide a substance dispensing device having means to enable a full charge of a substance to be available for discharge preparatory to normal use of the device. Still another object of the present invention is to provide a dispensing device that is particularly suitable for use in transdermal application of substances.

SUMMARY OF THE INVENTION

In accordance with the present invention, these and other objects have now been realized by the discovery of a hand-held dispensing device for dispensing and applying a substance to the skin of a host, the device including a hollow body, a capsule mounted within the hollow body and including the substance therein, a nozzle having an outlet passage mounted within the hollow body in communication with the capsule, actuator means operable to cause a metered quantity of the substance to be dispensed from the capsule through the outlet passage of the nozzle, a shroud defining an exit space from the hollow body for receiving the substance emerging from the outlet passage, and closure means including a cap detachably mountable on the shroud to thereby selectively open or close the nozzle and thereby control escape of the substance from the capsule. In a preferred embodiment, the outer passage includes an exit end, and the closure means includes a closure member that is operative to close the outlet passage by engaging against a surface surrounding the exit end of the outlet passage. Preferably, the device includes force inducing means operative to apply a closing force to the closure member when the closure member is engaged with the surface surrounding the exit end of the outlet passage.

In accordance with one embodiment of the dispensing device of the present invention, the shroud includes a first end proximate to the nozzle and a second end distal from the nozzle, the second end including an open mouth, whereby the shroud confines the lateral spread of the substance during its passage from the nozzle to the open mouth. Preferably, the shroud is substantially conical and includes a progressively increasing size from the first end to the second end. In another embodiment, the cap is detachably mountable to the second end of the shroud and extends across and closes the open mouth when the closure means is operated to close the nozzle and does not extend across the open mouth when the closure means is operated to open the nozzle. In a preferred embodiment, the outlet passage includes an exit end, and the closure means includes an elongated closure member having a first end connected to the cap and a second end which is engageable with a surface associated with the exit end of the outlet passage to thereby close the nozzle. Preferably, the device includes force inducing means operative to apply a closing force to the elongated closure member when the elongated closure member is engaged with the surface associated with the exit end of the outlet passage. In a preferred embodiment, the cap includes a flexible end wall and the force inducing means includes the flexible end wall of the cap, the first end of the elongated closure member is connected to a mid region of the flexible end wall, and the flexible end wall is resiliently distorted so as to place the elongated closure member under compression when the cap is attached to the outer end of the shroud and the elongated closure member engages with the surface associated with the exit end of the outlet passage. Preferably, the cap is releasably snap engageable with the second end of the shroud.

In accordance with one embodiment of the dispensing device of the present invention, the distance between the nozzle and the second end of the shroud is predetermined, whereby the shroud may be used to regulate the distance between the nozzle and a target area onto which the substance is to be deposited. Preferably, the size of the open mouth is substantially equal to the size of the target area.

In accordance with another embodiment of the dispensing device of the present invention, the device includes guide means disposed adjacent the nozzle to receive at least part of the closure member and guide the closure member into correct engagement with the surface surrounding the exit end of the outlet passage when the closure means is mounted on the shroud to close the nozzle.

In accordance with another embodiment of the dispensing device of the present invention, the closure member includes flexible sealing means for engaging against the surface surrounding the exit end of the outlet passage. In a preferred embodiment, the flexible sealing means includes a flexible circular sealing lip that surrounds the exit end of the outlet passage when engaged with the surface surrounding the exit end of the outlet passage. Preferably, the closure member defines a cavity communicating with the exit end of the outlet passage when the flexible sealing means and the surface surrounding the exit end of the outlet passage are in engagement.

In accordance with the present invention, a hand-held device for dispensing and applying a substance to the skin of a host, has been invented, the device including a hollow body, a capsule mounted with the hollow body, a container for the substance forming part of the capsule and including the substance therein, a nozzle mounted within the hollow body, a pump operable to cause a metered quantity of the substance to be dispensed from the capsule through the nozzle in the form of a spray, an actuator mounted on the hollow body and being operable to cause operating of the pump, and absorption means locatable at a first location in alignment with the nozzle and at a second location out of alignment with the nozzle, whereby when the absorption means is at the first location it can absorb a pre-use quantity of the substance dispensed through the nozzle during at least a first of a series of operations of the actuator means, and when the absorption means is at the second location it can enable a full charge of the substance to be dispensed through the nozzle during a subsequent one of the series of operations of the actuator means. In a preferred embodiment, the device includes a cap member removably connectable to the dispensing device, the absorption means including an absorbent pad attached to the cap member, whereby when the cap member is connected to the dispensing device the absorbent pad is positioned in the path of the substance being dispensed through the nozzle. Preferably, the device includes a shroud defining an exit space for receiving the substance emerging from the nozzle, the shroud including a first end proximate to the nozzle and a second end distal from the nozzle, the second end including an open mouth, and the cap being removably connectable to the second end of the shroud.

In accordance with another embodiment of the dispensing device of the present invention, the device includes absorption means locatable at a first location in alignment with the nozzle and a second location out of alignment with the nozzle, whereby when the absorption means is in the first location it can absorb a pre-use quantity of the substance dispensed through the nozzle during at least the first of a series of operations of the actuator means, and when the absorption means is at the second location it can enable a full charge of the substance to be dispensed through the nozzle during a subsequent one of the series of operations of the actuator means. In a preferred embodiment, the absorption means includes an absorbent pad attached to the cap, whereby the absorbent pad is positioned in the path of the substance being dispensed through the nozzle when the cap is mounted on the shroud. More preferably, the absorbent pad is releasably attached to the cap.

In accordance with another embodiment of the dispensing device of the present invention, the shroud provides a non-vented wall around the exit space.

In accordance with another embodiment of the dispensing device of the present invention, the capsule is removably mounted within the hollow body. Preferably, the hollow body comprises a first part and a second part, each of the first and second parts defining a respective portion of a chamber within which the capsule is mounted.

In accordance with another embodiment of the dispensing device of the present invention, the actuator means includes a pump connected to the nozzle so as to be operable to withdraw the substance from the capsule and expel the withdrawn substance through the nozzle. In a preferred embodiment, the actuator means includes a button movably mounted on the hollow body and operable to cause operation of the pump.

In accordance with another embodiment of the dispensing device of the present invention, the actuator means includes a valve, the substance is pressurized, and the valve is selectively operable to permit dispersion of the substance in aerosol form from the nozzle. Preferably, the actuator means includes a button movably mounted on the hollow body and operable on a selective basis to open the valve.

In accordance with another embodiment of the dispensing device of the present invention, the substance includes a physiologically active agent in liquid solution, and a carrier selected to promote absorption of the active agent through the skin of a host. Preferably, the solution includes a volatile solvent. In another embodiment, the carrier is non-volatile, and preferably octyl salicylate.

In accordance with another embodiment of the dispensing device of the present invention, the surface surrounding the exit end of the outlet passage is a frusto-conical surface, and the closure member includes a substantially complementary surface engageable with the frusto-conical surface.

In accordance with another embodiment of the dispensing device of the present invention, the hollow body is adapted to be grasped by the hand of a user and includes a major axis that extends transverse to the fingers of the user where grasped, and the nozzle is disposed to dispense the substance in a lateral direction relative to the major axis. Preferably, the shroud provides a non-vented wall around the exit space.

In accordance with another embodiment of the dispensing device of the present invention, the pump is connected to the nozzle, whereby the pump is operable to withdraw the substance from the container and expel the withdrawn substance through the nozzle.

According to one aspect of the present invention there is provided a hand-held device for dispensing a substance and applying that substance to the skin of a host, the device including a hollow body, a substance capsule mounted within the body, a container for the substance forming part of the capsule, a spray nozzle having an outlet passage, actuator means connected to the interior of the container and being operable to cause a metered quantity of the substance to be dispensed through the outlet passage of the nozzle, a shroud defining a space for receiving the substance emerging from the outlet passage, and closure means including a cap detachably located on the shroud selectively operable to close or open the nozzle and thereby control escape of the substance from the capsule.

A transdermal spray applicator device according to the present invention may be charged with a substance in the form of a single-phase volatile/non-volatile liquid provided within a standard plastic and/or glass container (depending on the characteristics of the active ingredient). Manufacture of the device in one of its preferred forms is relatively straight-forward, amenable to simple scale-up, and uses "off-the-shelf" components for the primary pharmaceutical packaging. That contrasts with the complexities involved in manufacturing occlusive patch devices as described above.

In a preferred form of the device, the nozzle outlet communicates with a space defined within a shroud of suitable configuration and size. Such a shroud is particularly useful in circumstances involving transdermal application of a substance, because it can assist in ensuring that the dispensed substance is confined to the intended target area. It is preferred that the shroud provides a complete non-vented enclosure over the target area so as to reduce the risk of spray drift and consequent loss of some of the substance being dispensed. Furthermore, the shroud can function as a distance regulating device. That is, when the open mouth of the shroud engages a surface surrounding the intended target area, the distance between the target area and the outlet of the spray nozzle is preferably substantially equal to the ideal distance over which the substance should be sprayed on to the target area.

Reference to "non-vented" in the previous paragraph and other parts of this specification is not to be understood as demanding complete absence of exposure to the atmosphere. The preferred shroud is "non-vented" in the sense that it does not have openings deliberately formed through the side wall (e.g. as in the device of U.S. Pat. No. 6,113,008), or through the outer edge intended to engage against the surface surrounding the target area.

The nozzle closure means may be formed by or provided on a cap that is adapted to close the open mouth of the shroud when the device is not in use. By way of example, the closure means may include an elongated stem that extends outwards from a wall of the cap. The arrangement is such that the end of the stem remote from the cap wall is engageable within and/or around the nozzle outlet when the cap is in place on the shroud. It is preferred that the cap wall is flexible and is subjected to resilient distortion when the cap is attached to the shroud. The stress thereby generated within the cap wall tends to push the closure stem against the nozzle outlet and thereby maintain a suitable closing force between the stem and the outlet.

According to another aspect of the present invention, there is provided a substance dispensing device having means for enabling a full charge of a substance to be available within the delivery system of the device for discharge when the device is operated in a normal manner. In that regard, a "full charge" is to be understood as comprising a quantity of the substance substantially equal to the melted amount intended to be discharged form the device when operated in a correct manner.

A condition called "loss of prime" can occur in the delivery system while the device is not in use. One cause of such loss of prime is evaporation, particularly when volatile substances are being used. As a result, air occupies a space within the delivery system that was intended to be occupied by the substance. Thus, when the device is thereafter operated to discharge the substance, the quantity discharged will be less than the intended metered quantity.

In order to enable a full charge of the substance to be available for discharge, a device in accordance with a second aspect of the present invention may be provided with means for absorbing a pre-use quantity of the substance. Prior to normal use of the device, the absorption means is placed in alignment with the nozzle outlet, and the device is operated to cause a pre-use quantity of the substance to be directed onto the absorption means. The delivery system of the device is thereby primed in the sense that it thereafter contains a full charge of the substance. Removal of the absorbing means from exposure to the nozzle outlet enables the device to be operated to discharge the intended metered quantity of the substance.

The absorption means referred to above can be substituted for the closure means of the first described aspect of the invention. That is, it may not be necessary to provide a device with both the nozzle closure means and the priming means as described above. Each has the ability to control loss of prime so as to thereby improve the efficiency and effectiveness of substance dispensing devices, and is therefore useful in its own right. On the other hand, a device could incorporate both the closure means and the priming means if desired.

A device according to either aspect of the present invention as described above could be disposable or rechargeable. That is, in one form, the entire device may be discarded when the contents of the capsule are exhausted, whereas in another form the capsule may be removably mounted in the hollow body of the device so as to enable removal and replacement by a fully charged capsule.

Also, in a device according to either of the two described aspects of the present invention, the form of the actuator means may differ according to whether the substance is dispensed by means of a manually operable pump, or by an aerosol-type process. In the former case, the pump may form part of the actuator means. In the latter case the actuator means may include a valve that is operable to connect the nozzle to the pressurized contents of the substance container.

BRIEF DESCRIPTION OF THE DRAWINGS

Embodiments of the present invention are described in detail in the following detailed description which refers to the accompanying drawings. The drawings, however, are merely illustrative of how the present invention might be put into effect, so that the specific form and arrangement of the various features as shown is not to be understood as limiting on the invention.

FIG. 7 is a top, elevational, cross-sectional view of the dust cap shown in FIG. 5;

FIG. 8 is a top, elevational, partial, enlarged view of the terminal end of the dust cap stem of FIG. 7, and the surface with which that end cooperates; and FIG. 9 is a top, elevational, cross-sectional view of another form of dust cap that can be used with the device shown in FIGS. 1 to 3.

DETAILED DESCRIPTION

Figure 2:
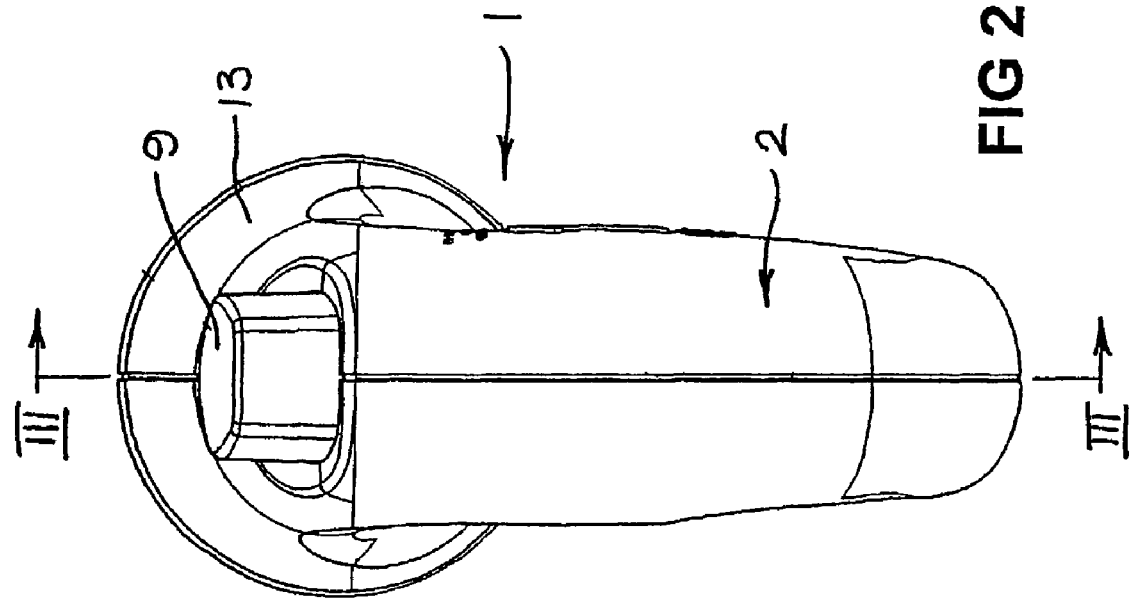
FIG. 2 is a rear, elevational view of the device shown by FIG. 1.

The example of the dispensing device 1 of the present invention shown in the accompanying drawings includes a hollow body 2 having a chamber 3 (FIG. 3) for receiving a substance capsule 4, which may be replaceable in some circumstances. The contents (the substance) of the capsule 4 will be selected to suit the intended use of the device 1. In the example shown, the capsule 4 includes a substance container 5 and a manually operable pump 6 (FIG. 3) for dispensing a metered quantity of the substance. Other arrangements could be adopted, such as an aerosol-type dispenser, in which event a suitable control valve (not shown) would be provided within the upper part, or some other convenient part, of the capsule 4.

In a preferred application of the device 1, the substance stored in the container 5 includes a physiologically active agent in liquid solution, and a carrier selected to promote absorption of the active agent through the skin of a host animal (eg., a human). The liquid solution preferably includes a volatile solvent, whereas the carrier is preferably non-volatile. In one application of the device the carrier may be octyl salicylate.

However the substance is driven to emerge from the device, it is preferably applied to a target area at relatively low volume levels. By way of example, the substance may be deposited in the range of 1 to 10 microliters per square centimeter of the target area.

Figure 1:
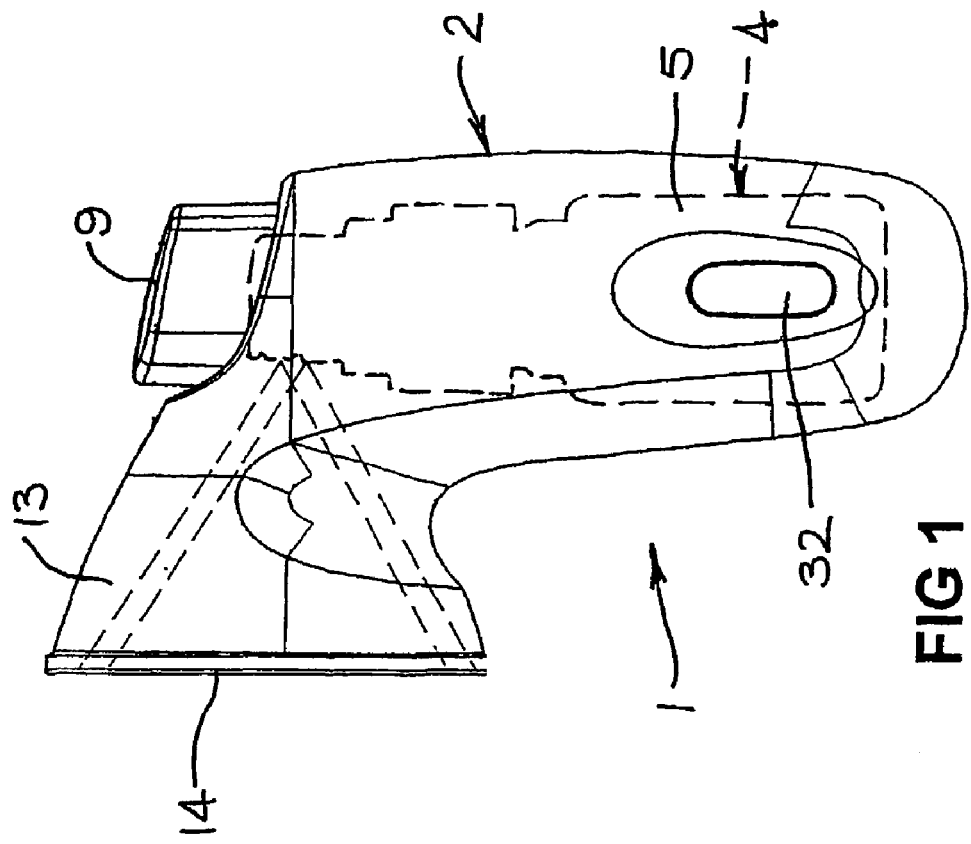
FIG. 1 is a side, elevational view of one form of dispensing device incorporating one embodiment of the present invention.
Figure 6:
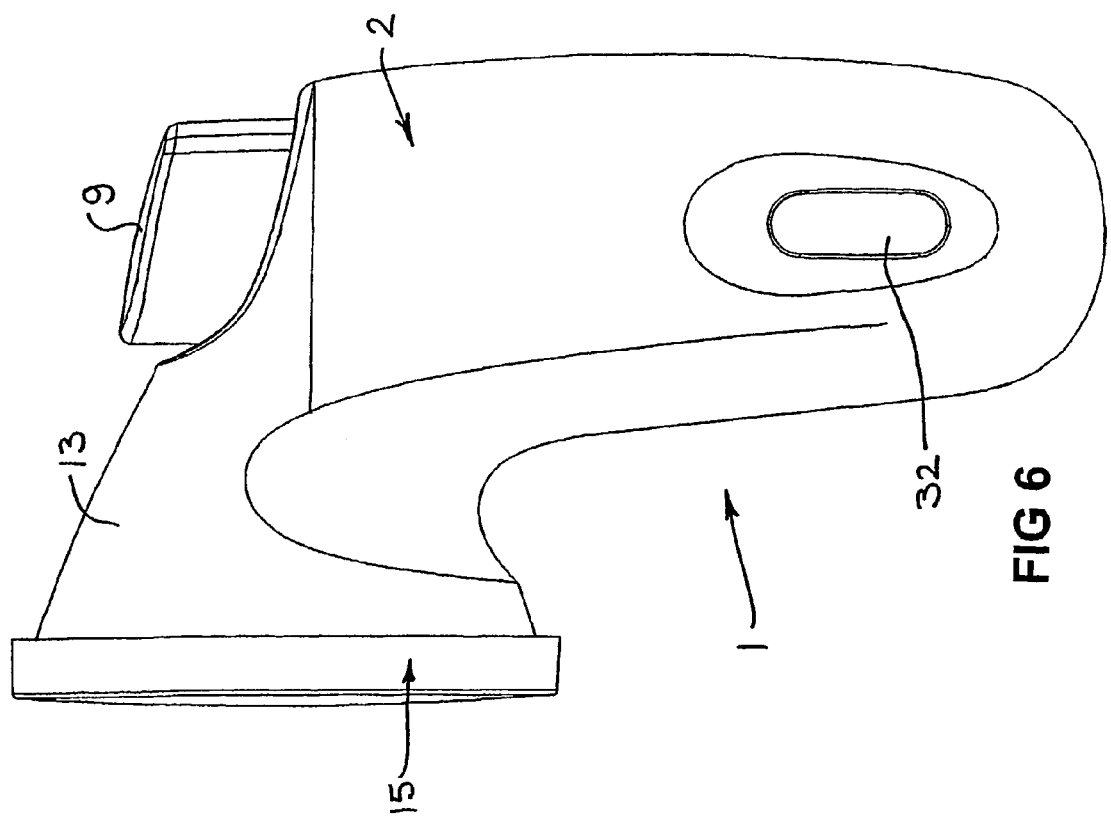
FIG. 6 is a side, elevational view of the device shown in FIG. 5.
Figure 4:
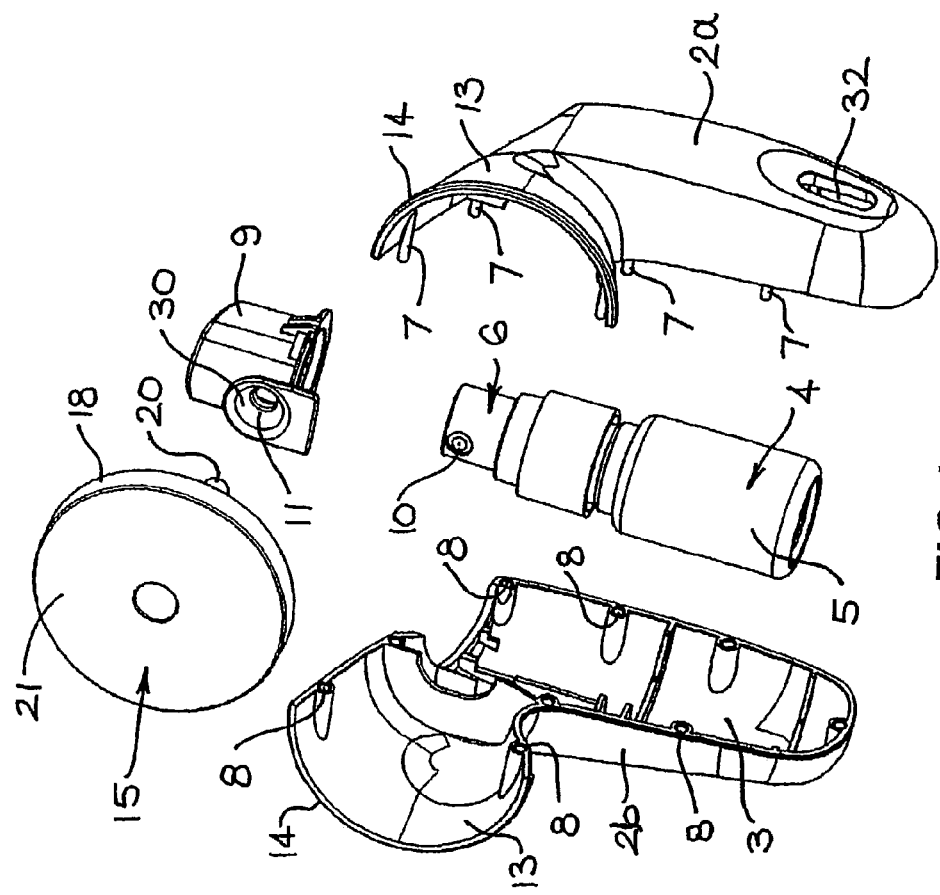
FIG. 4 is a front, perspective, exploded view of the device shown by FIG. 3.

It is preferred, as shown by FIG. 4, that the body 2 is formed of two separable parts 2a and 2b. Those parts combine to form the chamber 3 when they are connected together as shown by FIGS. 1 and 6, and any suitable means may be adopted to releasably connect the two parts 2a and 2b. In the arrangement shown, pins 7 provided on the part 2a are adapted to fit within complementary holes 8 provided in the part 2b (FIG. 4). The pins 7 and the holes 8 cooperate in a manner such as to resist inadvertent separation of the parts 2a and 2b.

Figure 5:
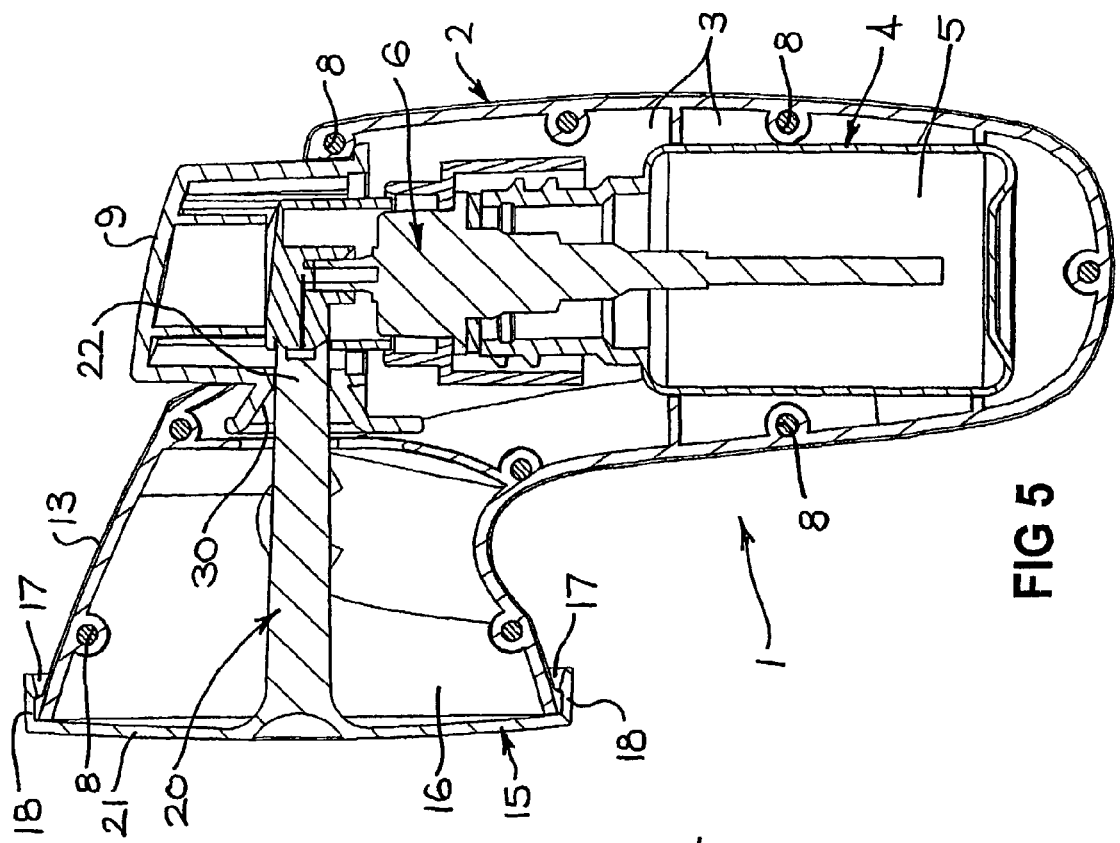
FIG. 5 is a side, elevational, cross-sectional view of the device shown in FIG. 3, but with a dust cap positioned over the outlet of the device.

In the particular arrangement shown, an actuator button 9 is movably mounted on the body 2 so as to be accessible at the upper end of the body 2 (FIGS. 1, 5 and 6). The button 9 cooperates with the pump 6 in a manner such that depression of the button 9 causes operation of the pump 6. When the pump 6 is operated, a quantity of the substance is withdrawn from the container 5 and is expelled through an outlet nozzle 10 associated with the pump 6, possibly in the form of a spray. In the arrangement shown, the button 9 locates over the outlet nozzle 10 and has an opening 11 aligned with the outlet passage 12 of the nozzle 10 so as to allow egress of the substance being dispensed. The pump 6 operates in a known manner to pressurize the contents of the substance container 5, and thereby force a metered quantity of the substance to be expelled through the nozzle 10.

A shroud 13, preferably of substantially conical form, may be connected to the side of the body 2 adjacent the nozzle 10. The shroud 13 is arranged to surround the substance spray emerging from the nozzle 10, and may serve to confine that spray so that all or most of the substance is deposited on the intended target area. In that regard, the shroud 13 is preferably non-vented as hereinbefore defined. The shroud 13 may also function as a distance regulator. That is, the distance between the nozzle 10 and the outer edge 14 of the shroud 13 may substantially correspond to the ideal distance over which the substance should be sprayed on to the target area. Such distance regulation may be particularly useful in circumstance where the device is being used for transdermal application of a substance.

Figure 3:
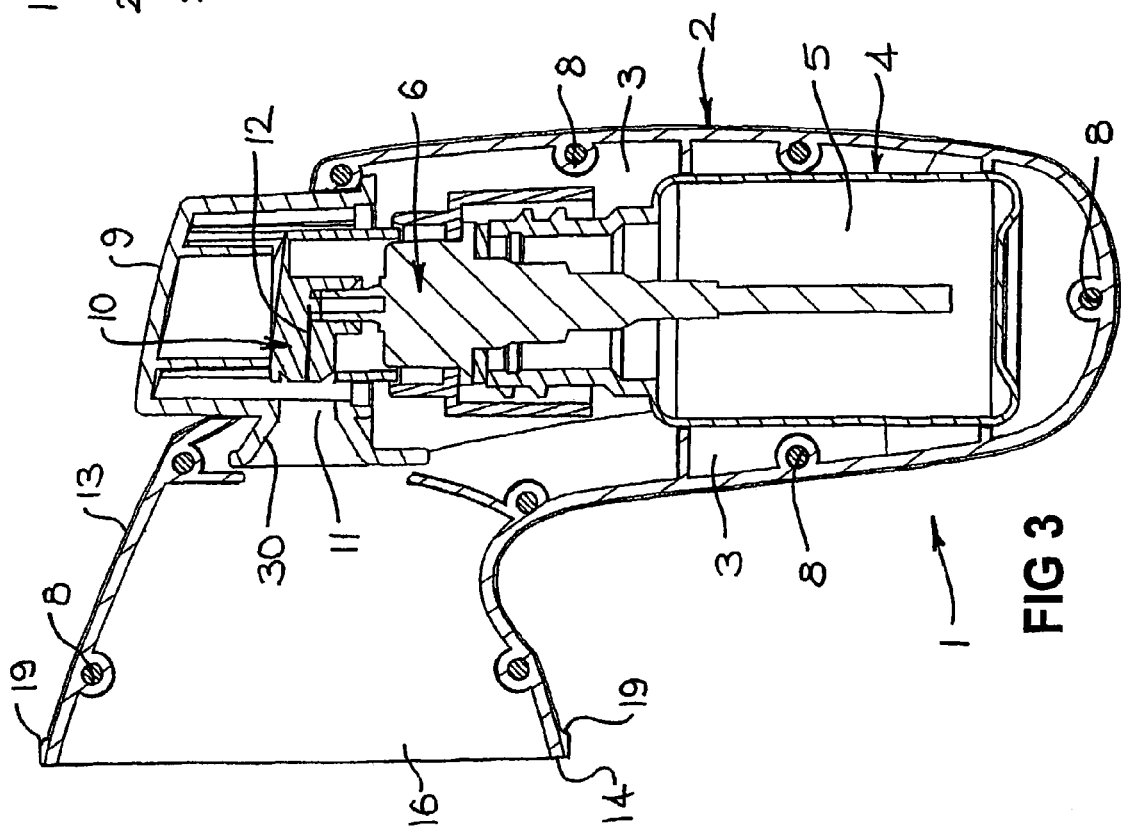
FIG. 3 is a side, elevational, cross-sectional view taken along line III—III of FIG. 2.

As shown in FIGS. 5 and 6, a protective cap 15 may be removably attached to the outer end of the shroud 13 so as to close the open mouth 16 (FIG. 3) of the shroud 13. The cap 15 is removed when the pump 6 is to be operated, and is replaced when the pump 6 is not in use. Any suitable means may be employed to enable releasable attachment of the cap 15. One option is to provide for snap engagement between the cap 15 and the shroud 13. By way of example, a circumferential rib 17 or lugs formed on an inner surface of a side wall 21 of the cap 15 may snap engage with an external circumferential rib 19 formed on the shroud 13 (FIG. 3).

In the arrangement shown by FIGS. 4 to 6, the dispensing device 1 is provided with means for closing the nozzle 10 when the device is not in use. Any suitable means may be used for that purpose. In the arrangement shown by FIGS. 4, 5 and 6, however, the nozzle closure means includes a member 20 attached to the end wall 21 of the cap 15. Preferably, as shown, the member 20 is in the form of an elongated stem extending axially of the cap 15 in the same direction as the side wall 21. The length of the member 20 is such as to enable the outer terminal end 22 to engage around and/or within the outlet of the nozzle 10 when the cap 15 is properly in place on the shroud 13.

According to the preferred arrangement shown, the end wall 21 of the cap 15 is flexible, and the length of the member 20 is such as to cause the wall 21 to flex outwardly when the cap 15 is properly located on the shroud 13. That is, when the stem end 22 engages within or around the outlet of the nozzle 10, proper cooperative engagement between the ribs 17 and 19 cannot be achieved unless the wall 21 is caused to flex outwardly. That outward flexing is indicated, in possibly exaggerated form, by the broken line in FIG. 7. As the wall 21 flexes outwardly, it undergoes resilient distortion such that internal stress is developed within the wall 21. The resilience of the wall 21 is such that it tends to return to the undistorted state and thereby relieve the internal stress, but such recovery is prevented by the column strength of the member 20. The member 20 is thereby placed under compression and as a result imposes a closing force between the end 22 of the member 20 and the nozzle 10. The degree of flexing is preferably predetermined to impose a suitable closing force between the end 22 of the member 20 and the nozzle 10.

FIG. 7 shows the end wall 21 having an outwardly bowed configuration when in the unstressed condition. That is not essential. By way of example, the wall 21 could be flat as shown by FIG. 9, when in the unstressed condition.

The effectiveness of the seal between the stem end 22 and the nozzle 10 may be enhanced by providing sealing means, such as resilient sealing means, at the end 22. Alternatively, as shown by FIGS. 7 and 8, the sealing means may include a relatively thin flexible circular sealing lip 23 extending generally in the axial direction of the member 20. Other types of sealing means could be adopted. Also, the sealing means may be provided on the nozzle 10 rather than the member 20, or may be provided on both the member 20 and the nozzle 10.

FIG. 8 illustrates a sealing arrangement between the member 20 and the nozzle 10 that has been found satisfactory in practice. As shown, the end 22 of the member 20 is shaped to provide the sealing lip 23. The radially inner surface 24 of the lip 23 slopes inwardly and rearwardly to provide a sealing face that functions as hereinafter described. A cavity 25 is formed within the member 20 directly behind the lip 23, and that cavity functions as hereinafter described.

As also shown by FIG. 8, the nozzle passage 12 emerges through a surface 26 of the nozzle 10 that is in opposed relationship with the terminal end of the member 20. The surface 26 is surrounded by a frusto-conical surface 27 that is substantially complementary to the surface 24 of the sealing lip 23. A recess 28 for receiving the sealing lip 23 is defined between the frusto-conical surface 27 and a surrounding cylindrical surface 29. The diameter of the surface 29 is preferably such that clearance exists between that surface and the stem end 22 when the stem end 22 is located within the recess 28.

Closure of the nozzle 10 occurs when the surface 24 of the sealing lip 23 is pressed against the nozzle surface 27. As previously stated, the sealing lip 23 has a degree of flexibility, and that serves to ensure that satisfactory sealing engagement occurs between the surfaces 24 and 27.

The cavity 25 has been found useful because of the air space it provides beyond the nozzle surface 26. In the absence of such an air space it has been found that the stored substance tends to weep out of an exit end of the nozzle passage 12, possibly due to capillary action. It will be appreciated that other arrangements could be adopted to combat that loss of substance. Also, sealing configurations other than that particularly shown by FIG. 8 could be adopted.

Guide means may be provided to guide the end 23 of the member 20 into the correct position of engagement with the nozzle 10. Such guide means can also serve to minimize damage to the sealing lip 23 when the cap 15 is being placed on the shroud 13. According to the arrangement shown, the guide means includes a frusto-conical guide passage 30 that extends outwards from and surrounds the outlet opening 11 of the actuator button 9 (FIGS. 3 and 4). As best seen in FIG. 3, the passage 30 increases in cross-sectional size in a direction away from the opening 11.

Instead of using nozzle closure means as described above, the device 1 may be provided with means to permit the delivery system of the pump 6 to be primed in preparation for use to dispense a metered quantity of the substance. One possible form of priming means is shown in FIG. 9. In that example, an absorbent pad or wad 31 is provided on the inside surface of the cap end wall 21, which need not be bowed outwards as shown by FIG. 7. Priming of the pump 6 is achieved by operating the pump 6 to spray a quantity of the stored substance on to the wad 31 while the cap 15 is located over the open mouth of the shroud 13. It is usually necessary to fully depress the button 9 at least once to achieve satisfactory priming, and two or more full depressions may be required. The priming operation can be carried out while the cap 15 is secured to the shroud 13, or while it is held removed from the shroud 13. In the latter case, however, the cap 15 is preferably held relatively close to the outer end of the shroud 13. The wad 31 may be removable from the cap 15 so as to enable replacement by a fresh wad, if and when necessary.

If desired, a viewing window 32 may be provided in a side of the body 2 so as to enable the user to see when the quantity of the substance in the capsule 4 is getting low (FIGS. 4 and 6).

It will be apparent from the foregoing description that a dispensing device according to the present invention has the ability to ensure that a full metered dose of the substance is discharged each time the device is operated. According to one aspect of the present invention, that result is achieved by effectively closing the outlet nozzle when the device is not in use. According to another aspect, the result is achieved by providing means whereby the pump can be primed preparatory to normal use.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A hand-held dispensing device for dispensing and applying a substance to the skin of a host, said device including a hollow body, a capsule mounted within said hollow body and including said substance therein, a nozzle having an outlet passage mounted within said hollow body in communication with said capsule, actuator means operable to cause a metered quantity of said substance to be dispensed from said capsule through said outlet passage of said nozzle, a shroud defining an exit space from said hollow body for receiving said substance emerging from said outlet passage, and closure means including a cap detachably mountable on said shroud to thereby selectively open or close said nozzle and thereby control escape of said substance from said capsule, said outlet passage including an exit end, and said closure means including a closure member that is operative to close said outlet passage by engaging against the surface surrounding said exit end of said outlet passage.

2. A dispensing device according to claim 1 including force inducing means operative to apply a closing force to said closure member when said closure member is engaged with said surface surrounding said exit end of said outlet passage.

3. A dispensing device according to claim 1, wherein said shroud includes a first end proximate to said nozzle and a second end distal from said nozzle, said second end including an open mouth, whereby said shroud confines the lateral spread of said substance during its passage from said nozzle to said open mouth.

4. A dispensing device according to claim 3, wherein said shroud is substantially conical and includes a progressively increasing size from said first end to said second end.

5. A dispensing device according to claim 3, wherein said cap is detachably mountable to said second end of said shroud and extends across and closes said open mouth when said closure means is operated to close said nozzle and does not extend across said open mouth when said closure means is operated to open said nozzle.

6. A dispensing device according to claim 5, wherein said outlet passage includes an exit end, and said closure means includes an elongated closure member having a first end connected to said cap and a second end which is engageable with a surface associated with said exit end of said outlet passage to thereby close said nozzle.

7. A dispensing device according to claim 6, including force inducing means operative to apply a closing force to said elongated closure member when said elongated closure member is engaged with said surface associated with said exit end of said outlet passage.

8. A dispensing device according to claim 7, wherein said cap includes a flexible end wall and said force inducing means includes said flexible end wall of said cap, said first end of said elongated closure member is connected to a mid region of said flexible end wall, and said flexible end wall is resiliently distorted so as to place said elongated closure member under compression when said cap is attached to said outer end of said shroud and said elongated closure member engages with said surface associated with said exit end of said outlet passage.

9. A dispensing device according to claim 8, wherein said cap is releasably snap engageable with said second end of said shroud.

10. A dispensing device according to claim 5, wherein the distance between said nozzle and said second end of said shroud is predetermined, whereby said shroud may be used to regulate the distance between said nozzle and a target area onto which said substance is to be deposited.

11. A dispensing device according to claim 10, wherein the size of said open mouth is substantially equal to the size of said target area.

12. A dispensing device according to claim 1, including guide means disposed adjacent said nozzle to receive at least part of said closure member and guide said closure member into correct engagement with said surface surrounding said exit end of said outlet passage when said closure means is mounted on said shroud to close said nozzle.

13. A dispensing device according to claim 1, wherein said closure member includes flexible sealing means for engaging against said surface surrounding said exit end of said outlet passage.

14. A dispensing device according to claim 13, wherein said flexible sealing means includes a flexible circular sealing lip that surrounds said exit end of said outlet passage when engaged with said surface surrounding said exit end of said outlet passage.

15. A dispensing device according to claim 14, wherein said closure member defines a cavity communicating with said exit end of said outlet passage when said flexible sealing means and said surface surrounding said exit end of said outlet passage are in engagement.

16. A dispensing device according to claim 1, including absorption means locatable at a first location in alignment with said nozzle and a second location out of alignment with said nozzle, whereby when said absorption means is in said first location it can absorb a pre-use quantity of said substance dispensed through said nozzle during at least the first of a series of operations of said actuator means, and when said absorption means is at said second location it can enable a full charge of said substance to be dispensed through said nozzle during a subsequent one of said series of operations of said actuator means.

17. A dispensing device according to claim 16, wherein said absorption means includes an absorbent pad attached to said cap, whereby said absorbent pad is positioned in the path of said substance being dispensed through said nozzle when said cap is mounted on said shroud.

18. A dispensing device according to claim 17, wherein said absorbent pad is releasably attached to said cap.

19. A dispensing device according to claim 1, wherein said shroud provides a non-vented wall around said exit space.

20. A dispensing device according to claim 1, wherein said capsule is removably mounted within said hollow body.

21. A dispensing device according to claim 1, wherein said hollow body comprises a first part and a second part, each of said first and second parts defining a respective portion of a chamber within which said capsule is mounted.

22. A dispensing device according to claim 1, wherein said actuator means includes a pump connected to said nozzle so as to be operable to withdraw said substance from said capsule and expel said withdrawn substance through said nozzle.

23. A dispensing device according to claim 22, wherein said actuator means includes a button movably mounted on said hollow body and operable to cause operation of said pump.

24. A dispensing device according to claim 1, wherein said actuator means includes a valve, said substance is pressurized, and said valve is selectively operable to permit dispersion of said substance in aerosol form from said nozzle.

25. A dispensing device according to claim 24, wherein said actuator means includes a button movably mounted on said hollow body and operable on a selective basis to open said valve.

26. A dispensing device according to claim 1, wherein said substance includes a physiologically active agent in liquid solution, and a carrier selected to promote absorption of said active agent through the skin of a host.

27. A dispensing device according to claim 26, wherein said solution includes a volatile solvent.

28. A dispensing device according to claim 26, wherein said carrier is non-volatile.

29. A dispensing device according to claim 28, wherein said carrier is octyl salicylate.

30. A dispensing device according to claim 1, wherein said surface surrounding said exit end of said outlet passage is a frusto-conical surface, and said closure member includes a substantially complementary surface engageable with said frusto-conical surface.

31. A dispensing device according to claim 1, wherein said hollow body is adapted to be grasped by the hand of a user and includes a major axis that extends transverse to the fingers of said user where grasped, and said nozzle is disposed to dispense said substance in a lateral direction relative to said major axis.

32. A hand-held dispensing device for dispensing and applying a substance to the skin of a host, said device including a hollow body, a capsule mounted with said hollow body, a container for said substance forming part of said capsule and including said substance therein, a nozzle mounted within said hollow body, a pump operable to cause a metered quantity of said substance to be dispensed from said capsule through said nozzle in the form of a spray, an actuator mounted on said hollow body and being operable to cause operating of said pump, and absorption means locatable at a first location in alignment with said nozzle and at a second location out of alignment with said nozzle, whereby when said absorption means is at said first location it can absorb a pre-use quantity of said substance dispensed through said nozzle during at least a first of a series of operations of said actuator means, and when said absorption means is at said second location it can enable a full charge of said substance to be dispensed through said nozzle during a subsequent one of said series of operations of said actuator means.

33. A dispensing device according to claim 32, including a cap member removably connectable to said dispensing device, said absorption means including an absorbent pad attached to said cap member, whereby when said cap member is connected to said dispensing device said absorbent pad is positioned in the path of said substance being dispensed through said nozzle.

34. A dispensing device according to claim 33, including a shroud defining an exit space for receiving said substance emerging from said nozzle, said shroud including a first end proximate to said nozzle and a second end distal from said nozzle, said second end including an open mouth, and said cap being removably connectable to said second end of said shroud.

35. A dispensing device according to claim 34, wherein said shroud provides a non-vented wall around said exit space.

36. A dispensing device according to claim 32, wherein said pump is connected to said nozzle, whereby said pump is operable to withdraw said substance from said container and expel said withdrawn substance through said nozzle.

37. A dispensing device according to claim 32, wherein said substance includes a physiologically active agent in liquid solution, and a carrier selected to promote absorption of said active agent through the skin of a host.

38. A dispensing device according to claim 32, wherein said surface surrounding said exit end of said outlet passage is a frusto-conical surface and said closure member includes a substantially complementary surface engageable with said frusto-conical surface.

39. A dispensing device according to claim 32, wherein said hollow body is adapted to be grasped by the hand of a user and includes a major axis that extends transverse to the fingers of said user where grasped, and said nozzle is disposed to dispense said substance in a lateral direction relative to said major axis.

\* \* \* \* \*

UNITED STATES PATENT AND TRADEMARK OFFICE
CERTIFICATE OF CORRECTION

PATENT NO. : 6,978,945 B2
DATED : December 27, 2005
INVENTOR(S) : Kon Euan Wong and Mark Simon Bayly It is certified that error appears in the above-identified patent and that said Letters Patent is hereby corrected as shown below:

Title page,
Item [75], Inventors, delete "Waverly" and insert -- Waverley --.

Column 13,
Line 3, delete "1" and insert -- 20 --.

Signed and Sealed this

Second Day of May, 2006

JON W. DUDAS
*Director of the United States Patent and Trademark Office*